(12) United States Patent
Auerbach

(10) Patent No.: US 11,865,070 B2
(45) Date of Patent: Jan. 9, 2024

(54) PRIMARY PACKAGING CONTAINERS FOR PHARMACEUTICAL SUBSTANCES AND METHODS OF MAKING

(71) Applicant: SCHOTT PHARMA SCHWEIZ AG, St. Gallen (CH)

(72) Inventor: Judith Auerbach, Niederteufen (CH)

(73) Assignee: SCHOTT PHARMA SCHWEIZ AG, St. Gallen (CH)

( * ) Notice: Subject to any disclaimer, the term of this patent is extended or adjusted under 35 U.S.C. 154(b) by 691 days.

(21) Appl. No.: 16/576,871

(22) Filed: Sep. 20, 2019

(65) Prior Publication Data

US 2020/0100985 A1 Apr. 2, 2020

(30) Foreign Application Priority Data

Sep. 28, 2018 (DE) .......................... 102018124115.1

(51) Int. Cl.
  *A61J 1/06* (2006.01)
  *A61J 1/14* (2023.01)
  *C08L 23/02* (2006.01)
  *B65D 51/00* (2006.01)

(52) U.S. Cl.
  CPC ............. *A61J 1/062* (2013.01); *A61J 1/1406* (2013.01); *B65D 51/002* (2013.01); *C08L 23/025* (2013.01)

(58) Field of Classification Search
  CPC ....... A61J 1/062; A61J 1/1406; B65D 51/002; C08L 23/025
  See application file for complete search history.

(56) References Cited

U.S. PATENT DOCUMENTS

| 2,533,165 A * | 12/1950 | Hagedorn .............. A61J 1/1406 206/438 |
| 6,681,475 B2 * | 1/2004 | Thibault .............. B65D 51/002 53/410 |
| 2012/0067888 A1 * | 3/2012 | Kawachi .............. B65D 51/002 220/233 |
| 2012/0091026 A1 * | 4/2012 | Chacornac .............. A61K 39/05 53/471 |

(Continued)

FOREIGN PATENT DOCUMENTS

| DE | 102011112516 | 3/2013 |
| EP | 0364783 | 4/1990 |

(Continued)

OTHER PUBLICATIONS

ISO 868, "Plastics and ebonite—Determination of indentation hardness by means of a durometer (Shore hardness)", Third Edition, Mar. 1, 2003, 12 pages.

(Continued)

*Primary Examiner* — Ariana Zimbouski
(74) *Attorney, Agent, or Firm* — Ruggiero McAllister & McMahon LLC

(57) ABSTRACT

A primary packaging container for pharmaceuticals is provided. The container includes a hollow body, an opening, and a closure. The hollow body has an opening and is made of a cycloolefin polymer or a cycloolefin copolymer. The closure has a puncture region. The closure closes the opening with the puncturing region at the opening. The puncturing region is configured to allow introduction of a cannula into the hollow body and resealing the hollow body upon withdraw of the cannula. The closure has an elastomer that is connected to the hollow body so as to be not separable in a non-destructive manner.

23 Claims, 5 Drawing Sheets

(56) References Cited

U.S. PATENT DOCUMENTS

2013/0144262 A1    6/2013   Kuhn
2014/0202980 A1    7/2014   Sattig
2015/0305977 A1*  10/2015   Spallek ................ A61J 1/1475
                                                              53/426
2020/0230024 A1*   7/2020   Wyler .................. B32B 27/322

FOREIGN PATENT DOCUMENTS

EP             1717161 A1 * 11/2006  ............ A61J 1/1406
WO     WO-2004018317 A2 *  3/2004  ............ A61J 1/1412

OTHER PUBLICATIONS

DIN EN ISO 8872, "Aluminium caps for transfusion, infusion and injection bottles-General requirements and test methods", Dec. 2003, 13 pages.
DIN ISO 13926-1, "Pen systems-Part 1: Glass cylinders for pen-injectors for medical use", Oct. 2005, 7 pages.
ISO 11608-1, "Needle-based injection systems for medical use-Requirements and test methods-Part 1: Needle-based injection systems", Third Edition, Dec. 15, 2014, 52 pages.
ISO 11040-1, "Prefilled syringes—Part 1: Glass cylinders for dental local anaesthetic cartridges", Second Edition, Dec. 1, 2015, 12 pages.
ISO 11040-3, "Prefilled syringes—Part 3: Seals for dental local anaesthetic cartridges", Second Edition, Jan. 15, 2012, 12 pages.
DIN EN ISO 8871-1, "Elastometric parts for parenterals and for devices for pharmaceutical use-Part 1: Extractables in aqueous autoclavates", Nov. 2004, 32 pages.

* cited by examiner

PRIMARY PACKAGING CONTAINERS FOR PHARMACEUTICAL SUBSTANCES AND METHODS OF MAKING

CROSS REFERENCE TO RELATED APPLICATIONS

This application claims benefit under 35 USC § 119 of German Application No. DE 10 2019 124 115.1 filed Sep. 28, 2019, the entire contents of which are incorporated herein by reference.

BACKGROUND

1. Field of the Invention

The invention relates to primary packaging containers for pharmaceutical substances and methods for making the primary packaging containers.

2. Description of Related Art

Pharmaceutical primary packaging containers such as vials and carpules are used for the sterile storage, and partially also directly in the subsequent administering, of pharmaceutical substances. The extraction of the pharmaceutical substance generally takes place via a cannula. For this, a corresponding puncture region in the closure of the primary packaging container is punctured. Whereas in the case of a vial, the pharmaceutical substance is generally firstly extracted with a syringe, the pharmaceutical substance can be administered directly from a carpule with the aid of a suitable injection device. Irrespective of the subsequent application, a sealed closure which guarantees sterility and, at the same time enables an easy extraction by container of a cannula, is of central importance for such primary packaging containers.

Pharmaceutical primary packaging containers such as vials and carpules are generally configured according to the prior art as described below. The primary packaging containers usually consist of a hollow body, which has a body, shoulder, neck, flanged rim, and opening. The hollow body can be made from various materials, inter alia glass, cycloolefin polymer or cycloolefin copolymer. In addition, mostly after filling with a pharmaceutical substance, a closure is mounted on the opening. The closure consists of two elements, a septum, and a crimp. The septum generally consists of a rubber and has a piercing region. The crimp is usually made from an aluminium alloy and has a central space for the piercing region. The closure is manufactured separately from the two elements. Corresponding closures for pharmaceutical primary packaging container are sufficiently known from the prior art and are regulated for example by ISO 8872:2003. The septum is connected with the hollow body by flanging of the crimp. Here, the septum is pressed on by the crimp and thereby the hollow body is connected with the closure in a form-fitting manner. The connection between hollow body and septum can be released by removal of the crimp non-destructively and in a residue-free manner. By renewed flanging of a crimp onto the hollow body, the connection can be re-established in the same quality using the same septum.

The prior art has the disadvantages which are described below. After the manufacture of the hollow body, the closure must be separately produced and mounted. Therefore, several elements and manufacturing steps are required for the production of the primary packaging container, whereby the cost of materials increases, the production becomes longer and more laborious and therefore is also more difficult to automate. Moreover, the use of different elements and manufacturing steps additionally has a disadvantageous effect. On the one hand, the likelihood of contaminating the primary packaging container with particles during the individual manufacturing steps is increased. On the other hand, the separate mounting of the closure carries the risk of including germs, so that the sealing surface of the closure must be laboriously sterilized. Furthermore, during the flanging of the closure, the danger exists that the primary packaging container is not tightly closed, and the pharmaceutical substance which is held can escape, or germs can penetrate from the exterior.

The type of fastening of the closure on the hollow body, in accordance with the prior art, is also disadvantageous. For the flanging of the closure, the hollow body must imperatively have a flanged rim; this is standardized for example for carpules by ISO 13926-1:2005-10. Therefore, deviations from the shape of the hollow body are not able to be realized, or are only able to be realized to a limited extent. Therefore, design changes of the primary packaging container, such as for example adaptations in the shape, size or the adding of form-fitting elements, are not able to be realized or are only able to be realized to a limited extent.

Especially in the case of primary packaging container, suitable for the direct administering of substances, such as carpules in a suitable injection device, design limitations in the shape lead to undesired dead volumes in the region of the opening. The plunger can only advance up to the start of the taper and can therefore not convey the remaining substance out from the primary packaging container. A reduction of the dead volume cannot be achieved, or can only be achieved to a limited extent, owing to the said shape restrictions.

Accordingly, it has been determined by the present application that there is a need for primary packaging containers and methods of making such containers that overcome, alleviate, and/or mitigate one or more of the aforementioned and other deleterious effects of prior art containers.

SUMMARY

It is an object of the present invention to overcome the disadvantages of the prior art and in particular to provide a primary packaging container for pharmaceutical substances which reduces the risk of an inclusion of particles or germs and which minimizes the manufacturing expenditure, to provide a corresponding production method of the primary packaging container, and to provide an apparatus having the primary packaging container with the pharmaceutical substance therein. In addition, it is an object of the invention to make possible an increased design freedom in the shape and size of the primary packaging container.

The primary packaging container according to the invention, preferably pharmaceutical primary packaging container, particularly preferably a vial or a carpule, for receiving a substance, preferably a pharmaceutical product, comprises a hollow body, wherein the hollow body comprises a cycloolefin polymer or a cycloolefin copolymer and has an opening, and a closure, wherein the closure closes the opening, comprises a normal elastomer and/or a thermoplastic elastomer and comprises a puncturing region for introducing a cannula into the hollow body, characterized in that the normal elastomer and/or the thermoplastic elastomer of the closure is not connected detachably in a non-destructive manner with the hollow body.

The hollow body can be embodied in the form of a vial or a carpule. Vials and carpules typically form a body, shoulder, neck, flanged rim and opening. The hollow body can also have a base. In addition to cycloolefin polymer or cycloolefin copolymer, the hollow body can also comprise other materials. Here, the cycloolefin polymer or the cycloolefin copolymer can contain additives. As additive, preferably a dye is used. Furthermore, the hollow body can also be manufactured from other materials. A multi-layered structure of the hollow body from various materials, such as manufactured for example by a sandwich injection moulding method, is also conceivable. The wall thickness of the hollow body is preferably 0.5 mm to 3 mm, but other wall thicknesses are also conceivable. The shape of the hollow body is limited only in the formation of an opening.

The substance which is held can be removed from the hollow body through the opening. In addition, the hollow body can comprise a second opening, for example for filling. A carpule generally has a second opening. Hereinafter, the second opening is not addressed further, and the term "opening" refers to the opening for removal, which is closed by the closure.

The closure is arranged on the opening. Here, the closure and the hollow body are discrete and are securely connected with one another without auxiliary container. A flanged-on crimp or comparable devices for fastening can be dispensed with.

In a preferred embodiment of the primary packaging container, the normal elastomer and/or the thermoplastic elastomer of the closure is connected with the hollow body in a materially bonded and/or micro-positive manner.

A materially bonded connection is to be understood to mean a connection which holds the connected components together by atomic and/or molecular forces. The atomic and molecular forces contain non-covalent interactions such as van der Waals interactions. A materially bonded connection cannot be separated in a non-destructive manner.

A micro-positive connection is to be understood to mean that the connected components engage into one another in the microscopic length range. Here the components do not become detached also with the absence of force transmission from the exterior, or with respect to one another. The connection of the components takes place in particular owing to the microscopic property of their surfaces. The surface structure can have pores, an increased roughness or targeted material unevenness or respectively material structurings. A micro-positive connection cannot be separated in a non-destructive manner.

In a preferred embodiment of the primary packaging container, the closure closes the hollow body in a sealed manner, preferably in a fluid-tight manner, particularly preferably in a gas-tight manner, wherein preferably the tightness remains after the introducing and taking out of a cannula through the puncturing region.

In a preferred embodiment of the primary packaging container, the hollow body and the closure are shaped such that the hollow body and the closure are connected with one another in a macro-positive manner.

A macro-positive connection is to be understood to mean that the connected components engage into one another in the macroscopic length range. Here, the components do not become detached also with the absence of force transmission from the exterior or with respect to one another. The connection of the components takes place in particular owing to macroscopic structural features of the components. The components can have indentations or convexities, which spatially hinder a detaching of the connection between the components. The macro-positive connection can supplement the materially bonded and/or micro-positive connection, in order to guarantee a sufficient sterile barrier.

In a preferred embodiment of the primary packaging container, at least a portion of the closure is under compressive stress at at least a portion of the contact surface between hollow body and closure.

The compressive stress onto the closure can result from a compression of the closure during the production of the primary packaging container. Owing to the elastic deformability of the closure, such a compressive stress occurs on the contact surfaces between hollow body and closure. Thereby, the connection and the tightness between hollow body and closure can be increased.

In a preferred embodiment of the primary packaging container the hollow body comprises on its outer side at least one form-fitting element for the form-fitting receiving of the primary packaging container in a device.

A form-fitting element is of importance in particular when the primary packaging container does not have a conventional flange. The form-fitting element can be arranged in the form of an indentation or convexity on the outer side of the hollow body. The form-fitting element is preferably arranged on the body of the hollow body. A single or a plurality of form-fitting elements can be present. The form-fitting element preferably consists of the same material as the hollow body and is preferably connected therewith in a macro-positive and/or micro-positive and/or materially bonded manner, or respectively is formed in one piece with the hollow body.

In a preferred embodiment of the primary packaging container, the closure covers at least portions of the outer side of the hollow body.

The covering of the surface with the closure material can inter alia increase the adhesion of the primary packaging container or intensify the connection with a device. Depending on the application of the primary packaging container, the closure can cover various portions of the outer side of the hollow body. Here, it is also conceivable that portions of the outer side of the hollow body are covered by separate closure material which is not connected with the actual closure.

In a preferred embodiment of the primary packaging container, the closure comprises at least a first layer, comprising a normal elastomer or a thermoplastic elastomer, and at least a second layer, comprising a normal elastomer or a thermoplastic elastomer. Here, the layers can be connected in a macro-positive and/or micro-positive and/or form-fitting manner.

A multi-layered closure enables the combination of various materials. Here, for the various layers, material-specific characteristics can be advantageously utilized. For example, the layer which is in contact with the substance which is being held can consist of a thermoplastic elastomer which is chemically inert with respect to the substance which is being held. A further adjoining layer can consist of a normal elastomer, which guarantees an increased tightness of the primary packaging container. For a closure made from several layers, various material combinations and numbers of layers are conceivable, which make use of different advantageous material characteristics. Through the use of several layers, in addition the material costs can be reduced.

The invention further comprises a method for the production of a primary packaging container comprising the following steps: Step a: optional preparing of at least one of the components, selected from hollow body and at least a portion of the closure; and Step b: producing the remaining components, selected from hollow body and at least a portion of the closure, in the injection moulding method, so that the closure closes the opening and a connection which is not detachable in a non-destructive manner is produced between the closure and the hollow body.

In a preferred embodiment of the method, the closure is prepared in Step a and the hollow body is produced in the injection moulding method in Step b, wherein a cycloolefin polymer or a cycloolefin copolymer is used, wherein the closure is injected around, so that preferably the closure and the hollow body are connected in a macro-positive manner.

For the production of the primary packaging container, the prior presentation of the closure, made by injection moulding or otherwise, is possible. A multi-part closure can also be presented. The presented closure is injected around, preferably with a cycloolefin polymer or a cycloolefin copolymer, and in so doing the hollow body is formed.

In a preferred embodiment of the method, in Step a the hollow body is prepared with the opening, optionally at least a portion of the closure is mounted onto the opening and in Step b the closure is formed completely in injection moulding with a thermoplastic elastomer, wherein preferably the closure and the hollow body are connected in a materially bonded and/or micro-positive manner.

For the production of the primary packaging container, the prior presentation of the hollow body, made by injection moulding or otherwise, is possible. In addition, a first portion of the closure, preferably a normal elastomer, can be presented. The presented parts are injected around, preferably with a thermoplastic elastomer, and in so doing the second portion of the closure is formed. Furthermore, the presented hollow body can also be injected around without the prior presentation of a portion of the closure. The presented hollow body is then injected around, preferably with a thermoplastic elastomer, and in so doing the entire closure is formed.

In a preferred embodiment of the method, in Step a optionally at least a portion of the closure is prepared and in Step b in multi-component injection moulding a cycloolefin polymer or a cycloolefin copolymer is injected for the production of the hollow body and a thermoplastic elastomer is injected for the complete formation of the closure, wherein preferably the closure and the hollow body are connected in a macro-positive and/or materially bonded and/or micro-positive manner.

Preferably, the entire primary packaging container, therefore hollow body and closure, is produced as a whole by multi-component injection moulding. In multi-component injection moulding, an injection moulded part can be produced from two or more different plastics. With multi-component injection moulding methods, it is possible to inject various plastics onto one another and to thus create a physical connection between the plastics. An injection moulding machine for multi-component injection moulding generally comprises two or more injection units and only one clamping unit. Furthermore, a pre-injected or otherwise prefabricated part can be inserted for injecting around. Different methods of multi-component injection moulding are conceivable. Thus, inter alia, also a multi-component method with sharply separated components is able to be carried out. Firstly, a preform is produced and is subsequently injected over with another component. In order to create space for the second component, different methods such as transfer technique, rotary/displacement technique or core retraction technique are conceivable. Multi-component injection moulding methods enable a favourably priced production with only one tool in one working step. In addition, compared to a conventional mounting of individual components, small positional tolerances are able to be implemented. Furthermore, the risk of a contamination is minimized.

In a preferred embodiment of the method, at least a portion of the closure is placed under compressive stress during or before the injection moulding method, so that the compressive stress is maintained after cooling of the injection-moulded material.

In the injection moulding, the closure undergoes a compression during injecting-around or injecting-on. The compression can be brought about by a component which exerts a pressure onto the closure. Preferably, the pressure-exerting component is removed again before completion of the injection moulding, with a maintaining of the compressive stress onto the closure.

In a preferred embodiment of the method, at least a portion of the contact surfaces between the hollow body and the closure is pretreated, preferably by activating, roughening or structuring of at least one surface, preferably of both surfaces.

The activation of the surface can take place inter alia by a flame, a plasma or a corona. A roughening of the surface can be carried out mechanically or chemically. The structuring of the surface can contain patterns such as grooves and grids, a chemical functionalizing or coatings. Here, both only the surface of the contact side of the hollow body or of the closure, or both surfaces can be pretreated.

The above-described and other features and advantages of the present disclosure will be appreciated and understood by those skilled in the art from the following detailed description, drawings, and appended claims.

DETAILED DESCRIPTION

Figure 1:
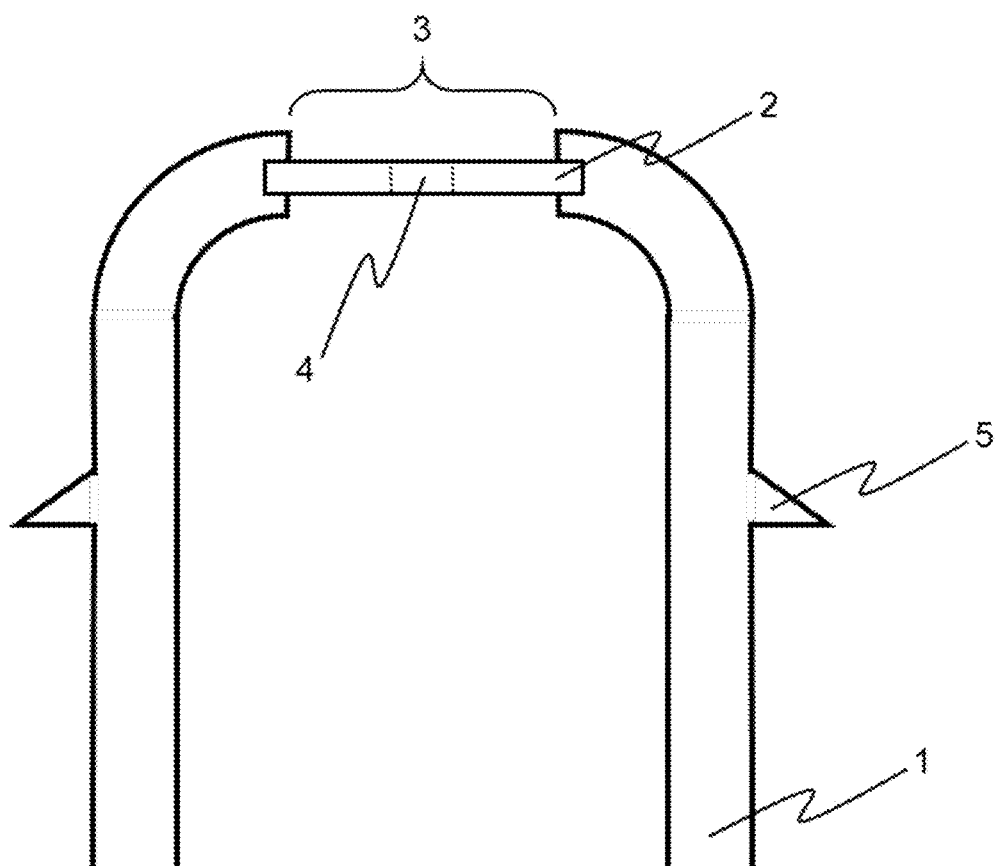
FIG. 1 is a cross-sectional view of a first embodiment of the primary packaging container according to the invention.

FIG. 1 shows a cross-sectional view through a first preferred embodiment of the primary packaging container according to the invention. The hollow body (1) comprises on its outer side a circumferential form-fitting element (5). The opening (3) of the hollow body (1) is closed by the closure (2). The hollow body (1) and the closure (2) are connected in a macro-positive manner. The closure (2) engages into an indentation (3a) on the inner side of the hollow body (1) in the region of the opening (3). The closure (2) comprises centrally a continuous volume element, which forms the puncturing region (4). The hollow body (1) consists of cycloolefin polymer or cycloolefin copolymer, and the closure (2) consists of a normal elastomer or of a thermoplastic elastomer. The wall thickness of the hollow body (1) is 0.5 mm to 3 mm. For the production of the first preferred embodiment, the closure (2) is prepared and in injection moulding is injected around with a cycloolefin polymer or with a cycloolefin copolymer for the formation of the hollow body (1).

Closure (2) is a normal elastomer, which is understood to mean chemically cross-linked polymers, which cannot be freed from one another again without breakdown. Normal elastomers can deform elastically under tensile and compressive load, but assume their original form again on removal of the load. In addition, normal elastomers display no thermoplastic behaviour under the application of heat and are therefore not able to be produced or shaped by injection moulding methods.

Thermoplastic elastomers are understood to mean cross-linked polymers which display, at room temperature, a comparable elastic deformation behaviour to normal elastomers. With the application of heat, however, thermoplastic elastomers are plastically deformable. The process is reversible and can be repeated by cooling and renewed heating. In terms of this application, a differentiation is therefore to be made between normal elastomers and thermoplastic elastomers. A thermoplastic elastomer can be, for example, a thermoplastic polyolefin elastomer, such as a cycloolefin polymer elastomer or a cycloolefin copolymer elastomer. Such a thermoplastic elastomer is available under the trade name TOPAS® Elastomer E-140.

The puncturing region (4) corresponds to a portion of the total volume of the closure (2). Here, the puncturing region (4) is preferably arranged in central position in the closure (2), in the form of a vertically oriented cylinder. Furthermore, preferably the transition within the closure (2) to the puncturing region (4) is marked homogeneously and not by a sharp boundary area.

In accordance with the invention, the connection between normal elastomer and/or thermoplastic elastomer of the closure and cycloolefin polymer or cycloolefin copolymer of the hollow body (1) is not separable in a non-destructive manner. "Not separable in a non-destructive manner" is to be understood to mean that after a separation of the hollow body (1) and the closure (2), a renewed connection of the same closure, in the same quality, in accordance with the original connection, is not possible. Moreover, the closure (2) cannot be separated from the hollow body (1) in a residue-free manner. On the separation, the hollow body (1) and the closure (2) are damaged, so that residues of the material remain on the other respective component.

The pharmaceutical product which is held can be, for example, a liquid or a solid. Moreover, the holding of a substance with a specific dosage of an active ingredient, for defined and easy administering or other application, is conceivable.

The design freedom in the shape of the hollow body (1) and closure (2) is distinctly increased for the primary packaging container according to the invention. Thereby, a flexible and individual use is possible in the most varied of devices and methods. Furthermore, design problems such as dead volumes on removal of substances can be eliminated or at least reduced. The primary packaging container according to the invention can be produced in a single process. For this reason, the cost of materials and the duration of production can be minimized. In addition, through the simplification of the production, a contamination of the primary packaging container or the inclusion of germs is prevented or at least reduced.

In a preferred embodiment of the primary packaging container, the closure (2) has in the puncturing region (4) a Shore hardness Shore-A of 20 to 70, wherein the load is maximally 30 N, preferably maximally 20 N, particularly preferably maximally 10 N.

The Shore hardness is a measurement for the hardness of materials. For conventional and thermoplastic elastomers, the Shore hardness is determined by container of the penetration depth of a spring-loaded steel pin. The determining of the Shore hardness for Shore-A can take place by container of ISO 868:2003-10 for a sample thickness of 4 mm, with a hold time of 3 s or 15 s and a load of 12.5 N.

The sealed closure (2) prevents substances or germs from arriving into the interior of the primary packaging container. Thereby, contaminations of the interior and/or of a substance which is held are prevented, and the sterility of the primary packaging container is guaranteed. Furthermore, the sealed closure (2) prevents a substance which is held from escaping out of the interior of the primary packaging container and enables an inert storage. The primary packaging container also retains these characteristics after the introducing of a cannula and only receives substances which are introduced via the cannula. A sealed closure (2) can be produced by the materially bonded and/or micro-positive and/or macro-positive applying of a normal elastomer and/or thermoplastic elastomer onto the opening of the hollow body (1).

In a preferred embodiment of the primary packaging container, the primary packaging container contains a substance, preferably a substance for therapeutic and/or diagnostic purposes, particularly preferably a single dose of the substance.

The primary packaging container can contain a substance such as an active ingredient or a pharmaceutical product. The primary packaging container preferably contains a specific dose of the active ingredient or of the pharmaceutical product. Thereby, the dosing or direct administering is distinctly simplified.

In a further preferred embodiment of the primary packaging container, between the closure (2) and hollow body (1), a clearance in the molecular range of values exists, preferably no gap exists.

A gap between the closure (2) and the hollow body (1) can be present in a micro-positive connection. However, the gap is limited to the order of magnitude of individual molecules or atoms, depending on the material of the closure (2) and of the hollow body (1).

Figure 2:
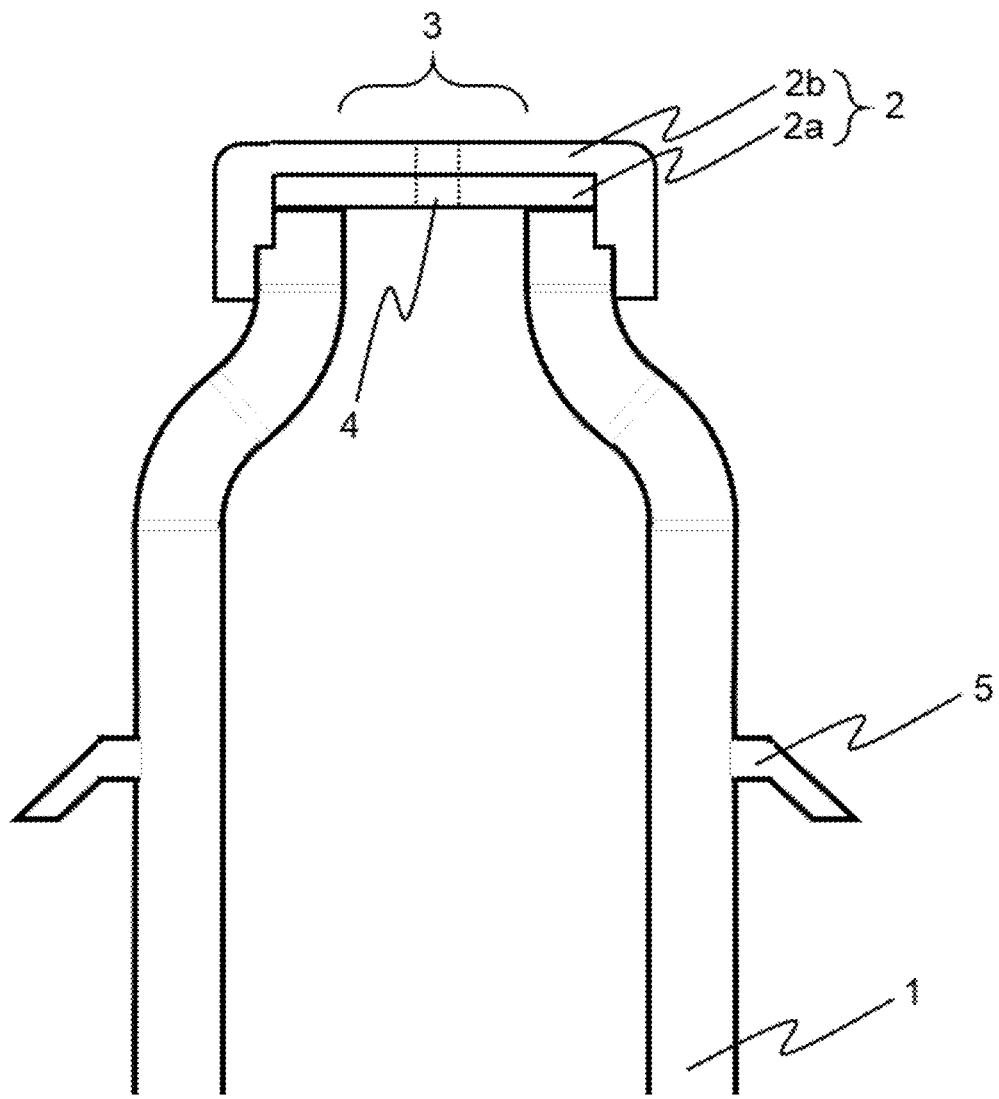
FIG. 2 is a cross-sectional view of a second embodiment of the primary packaging container according to the invention.

FIG. 2 shows a cross-sectional view through a second preferred embodiment of the primary packaging container according to the invention. The hollow body (1) comprises on its outer side at least two angled form-fitting elements (5). The opening (3) of the hollow body (1) is closed by the closure (2). The closure (2) comprises a lower (2a) and an upper (2b) closure layer. The lower closure layer (2a) is held in a micro-positive and macro-positive manner by the upper closure layer (2b) on the opening (3). The lower closure layer (2a) can be under an axial compressive stress on the contact surfaces to the hollow body (1) and the upper closure layer (2b). The upper closure layer (2b) and the hollow body (1) are connected in a materially bonded and/or micro-positive manner. The hollow body (1) comprises an indentation on the outer side in the region of the opening (3), in order to increase the contact surface with the upper closure layer (2b). The closure (2) comprises centrally a volume element passing through the lower (2a) and upper (2b) closure layer, which volume element forms the puncturing region (4). The hollow body (1) consists of cycloolefin polymer or cycloolefin copolymer. The lower closure layer (2a) consists of a normal elastomer and the upper closure layer (2b) consists of a thermoplastic elastomer. The wall thickness of the hollow body (1) is 0.5 mm to 3 mm. For the production of the second preferred embodiment, the lower closure layer (2a) is prepared and in multicomponent injection moulding a cycloolefin polymer or a cycloolefin copolymer is injected for the formation of the hollow body (1), and a thermoplastic elastomer is injected for the formation of the upper closure layer (2b). Alternatively, for the production of the second preferred embodiment, the hollow body (1) is prepared with the opening (3), the lower closure layer (2a) is prepared and is mounted onto the opening (3) and in injection moulding with a thermoplastic elastomer the upper closure layer (2b) is formed.

Figure 3:
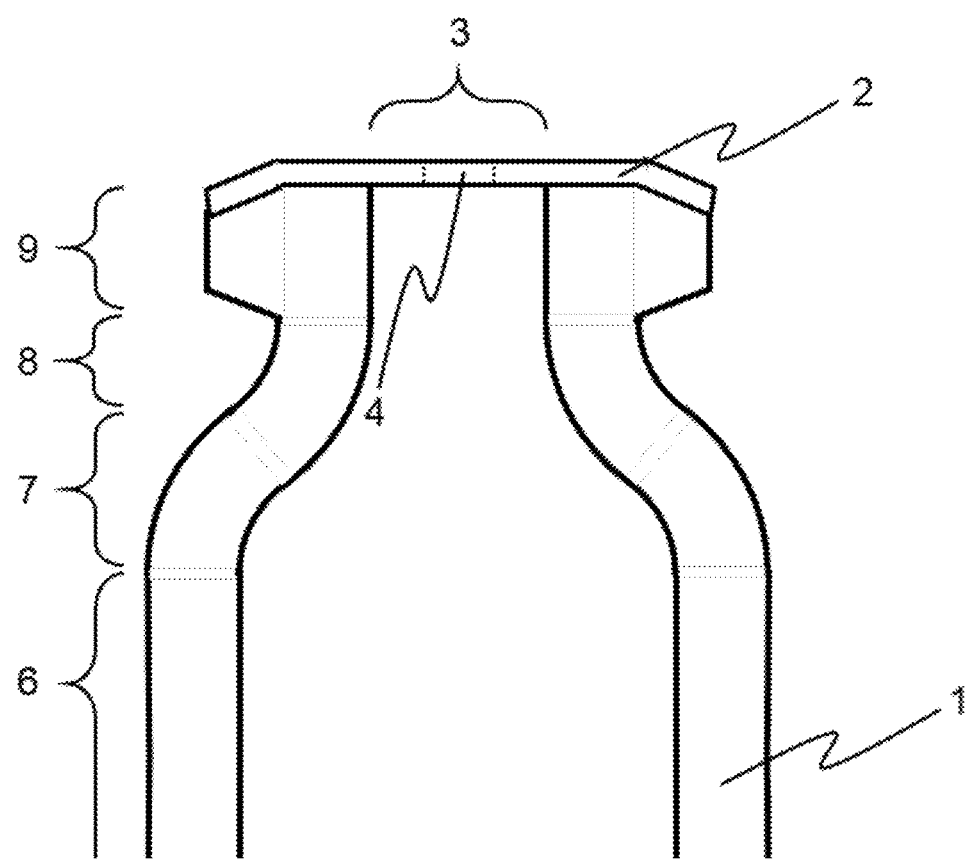
FIG. 3 is a cross-sectional view of a third embodiment of the primary packaging container according to the invention.

FIG. 3 shows a cross-sectional view through a third preferred embodiment of the primary packaging container according to the invention. The hollow body (1) comprises body (6), shoulder (7), neck (8) and flanged rim (9). The opening (3) of the hollow body (1) is closed by the closure (2). The hollow body (1) and the closure (2) are connected in a materially bonded and/or micro-positive manner. The closure (2) comprises centrally a continuous volume element, which forms the puncturing region (4). The hollow body (1) consists of cycloolefin polymer or cycloolefin copolymer, and the closure (2) consists of a thermoplastic elastomer. The wall thickness of the hollow body (1) is 0.5 mm to 3 mm. For the production of the third preferred embodiment, in multicomponent injection moulding a cycloolefin polymer or a cycloolefin copolymer is injected for the production of the hollow body (1) and a thermoplastic elastomer is injected for the formation of the closure (2).

In a further preferred embodiment of the primary packaging container, the hollow body (1) is configured in accordance with ISO 13926-1:2005-10, preferably with an angle between shoulder (7) and neck (8) of approximately 30°, an angle between neck (8) and flange (9) of 10° to 20° and an angle between flange (9) and opening (3) of 8° to 14°.

In a further preferred embodiment of the primary packaging container, the closure (2) is configured in accordance with ISO 8872:2003, preferably with a tensile strength of 100 N/mm$^2$ to 180 N/mm$^2$ and an elongation at break of at least 80 N/mm$^2$.

In a further preferred embodiment of the primary packaging container, the hollow body (1) is configured in accordance with ISO 11040-1:2015(E), preferably with an angle between shoulder (7) and neck (8) of 35° to 45°, an angle between neck (8) and flange (9) of 10° to 20° and an angle between flange (9) and opening (3) of 9° to 13°.

In a further preferred embodiment of the primary packaging container, the closure (2) is configured in accordance with ISO 11040-3:2012(E), preferably with a height of 1.3 mm to 1.5 mm or 1.45 mm to 1.95 mm, a diameter of 7.5 mm and a diameter of the puncturing region (4) of 3.0 mm.

The configuration of the hollow body (1) and of the closure (2) in accordance with the above-mentioned standards involve the advantage that the primary packaging container according to the invention can be used in existing and established devices and methods.

Figure 4:
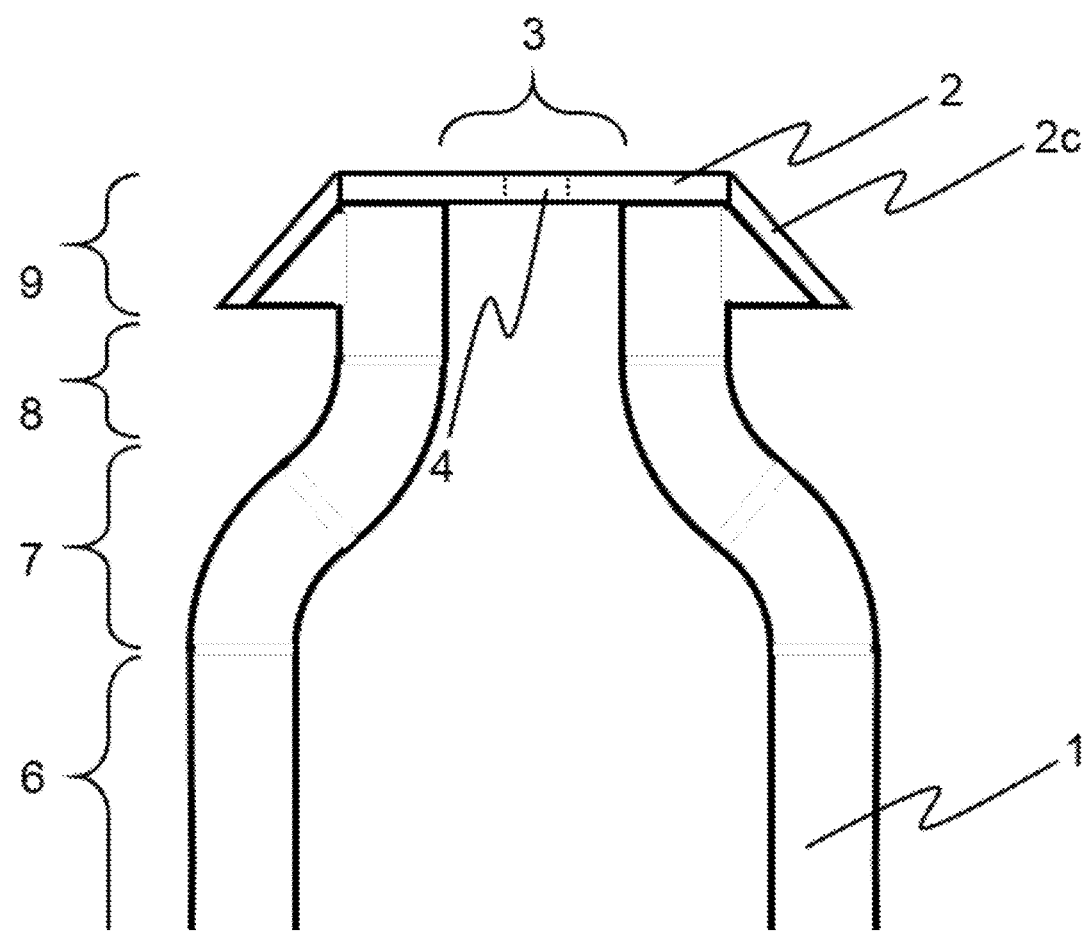
FIG. 4 is a cross-sectional view of a fourth embodiment of the primary packaging container according to the invention.

FIG. 4 shows a cross-sectional view through a fourth preferred embodiment of the primary packaging container according to the invention. The hollow body (1) comprises body (6), shoulder (7), neck (8) and flanged rim (9). The opening (3) of the hollow body (1) is closed by the closure (2). The hollow body (1) and closure (2) are connected in a materially bonded and/or micro-positive manner. The closure has a lateral closure layer (2c), which covers at least a portion of the flanged rim (9). The lateral closure layer (2c) increases the adhesion of the primary packaging container. The closure (2) comprises centrally a continuous volume element, which forms the puncturing region (4). The hollow body (1) consists of cycloolefin polymer or cycloolefin copolymer, and the closure (2) and the lateral closure layer (2c) consist of a thermoplastic elastomer. The wall thickness of the hollow body (1) is 0.5 mm to 3 mm. For the production of the fourth preferred embodiment, the hollow body (1) is prepared with the opening (3) and in injection moulding with a thermoplastic elastomer the closure (2) and the lateral closure layer (2c) are formed.

Figure 5A:
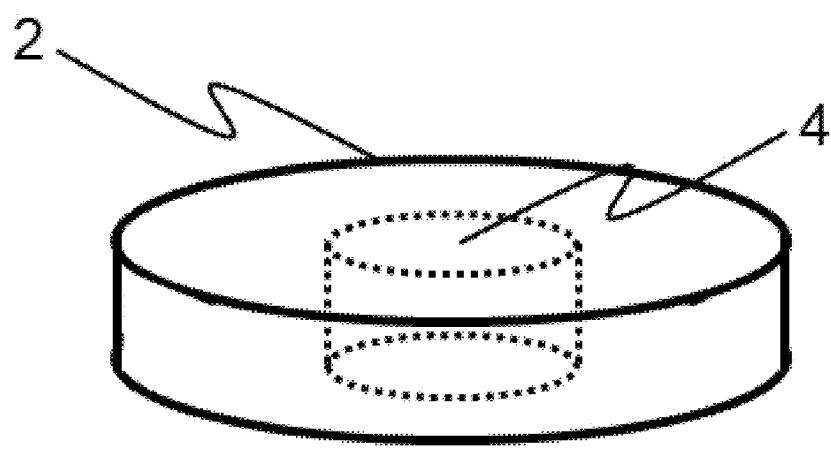
FIG. 5a diagrammatically illustrates of a first embodiment of the closure with puncturing region.
Figure 5B:
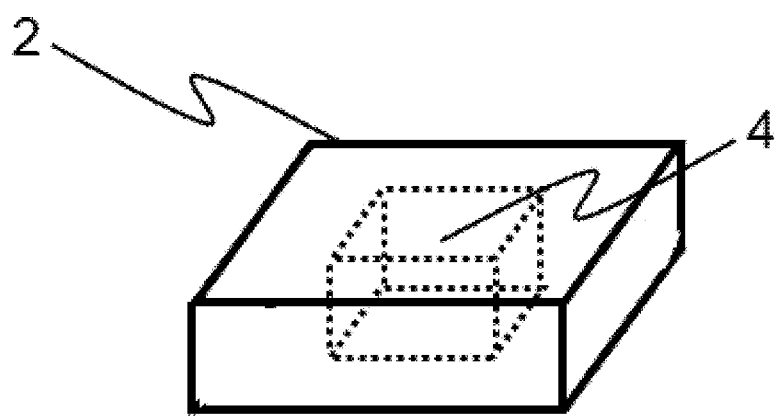
FIG. 5b diagrammatically illustrates of a second embodiment of the closure with puncturing region.

FIGS. 5a and 5b show respectively a diagrammatic illustration of the closure (2). The puncturing region (4) is formed as a partial volume of the closure (2). The puncturing region (2) extends from the upper side to the underside of the closure (2). This enables the introduction of a cannula into the hollow body of the primary packaging container. The closure can be configured in various ways. The forms illustrated by way of example by FIG. 5a and FIG. 5b are not to be understood to be limiting. Rather, the form conforms to the property and configuration of the hollow body in the region of the opening. The same applies to the puncturing region (4). The latter can be configured in various geometric shapes. Preferably, the puncturing region comprises a homogeneous transition and no sharp boundary area with respect to the remaining part of the closure (2).

The primary packaging container according to the invention differs fundamentally from the primary packaging container used hitherto with a closure made of a septum and aluminium crimp. Owing to the connection according to the invention between the hollow body and the closure, the shape of the hollow body can be adapted to the corresponding application in a variable manner. Thus, for example, dead volumes in the region of the opening of carpules and the losses resulting therefrom on removal of the substance which is being held can be ruled out or at least minimized.

Furthermore, the manufacture of the primary packaging container according to the invention is less complex and laborious compared to the primary packaging container used hitherto. The number of required components is less and the primary packaging container according to the invention can be manufactured in one process in injection moulding. With the manufacture in one process step, the risk of including foreign bodies or germs is ruled out or at least reduced. Overall, the production costs can be thereby reduced.

LIST OF REFERENCE NUMBERS 1 hollow body
2 closure
2a lower closure layer
2b upper closure layer
2c lateral closure layer
3 opening
4 puncturing region
5 form-fitting element
6 body
7 shoulder
8 neck
9 flanged rim

What is claimed is:

1. A primary packaging container for receiving a pharmaceutical product, comprising:
   a hollow body having an opening, the hollow body comprises a cycloolefin polymer or a cycloolefin copolymer; and
   a closure having a puncturing region, the closure closing the opening with the puncturing region at the opening, the puncturing region being configured to allow introduction of a cannula into the hollow body and resealing the hollow body upon withdrawal of the cannula, wherein the closure comprises a normal elastomer that connects the closure and the hollow body together so that the closure and the hollow body are not separable in a non-destructive manner and comprises a thermoplastic elastomer layer covering the normal elastomer in the puncture region.

2. The primary packaging container of claim 1, wherein the hollow body is a vial or a carpule.

3. The primary packaging container of claim 1, wherein the normal elastomer is connected in a materially bonded and/or micro-positive manner with the hollow body.

4. The primary packaging container of claim 1, wherein the normal elastomer and hollow body are connected so as to remain connected after the introduction and removal of the cannula through the puncturing region.

5. The primary packaging container of claim 4, wherein the normal elastomer closes the opening in a manner selected from a group consisting of sealed manner, a fluid-tight manner, and a gas-tight manner.

6. The primary packaging container of claim 1, wherein the hollow body and the closure are shaped such that the hollow body and the closure are connected with one another in a macro-positive manner.

7. The primary packaging container of claim 1, wherein the closure has at least a portion that is under compressive stress.

8. The primary packaging container of claim 1, wherein the normal elastomer has a Shore A hardness of 20 to 70 in the puncturing region.

9. The primary packaging container of claim 1, wherein the hollow body comprises an outer side having at least one form-fitting element, the form-fitting element being configured for receipt in a device.

10. The primary packaging container of claim 1, wherein the closure covers at least a portion of an outer side of the hollow body.

11. The primary packaging container of claim 1, wherein the thermoplastic elastomer layer covers at least a portion of an outer side of the hollow body.

12. The primary packaging container of claim 1, further comprising a single dose of a substance for therapeutic and/or diagnostic purposes.

13. The primary packaging container of claim 1, wherein the hollow body comprises an indentation on an inner side in a region of the opening, the normal elastomer being connected to the indentation.

14. The primary packaging container of claim 1, further comprising no gap between mating portions of the closure and hollow body.

15. The primary packaging container of claim 1, wherein the closure has a tensile strength of 100 N/mm$^2$ to 180 N/mm$^2$ and an elongation at break of at least 80 N/mm$^2$.

16. A primary packaging container for receiving a pharmaceutical product, comprising:
a hollow body having an opening, the hollow body comprises a cycloolefin polymer or a cycloolefin copolymer; and
a closure having a puncturing region, the closure closing the opening with the puncturing region at the opening, the puncturing region being configured to allow introduction of a cannula into the hollow body and resealing the hollow body upon withdrawal of the cannula,
wherein the closure comprises a normal elastomer that connects the closure and the hollow body together so that the closure and the hollow body are not separable in a non-destructive manner and comprises a thermoplastic elastomer layer over the normal elastomer, and
wherein the hollow body and the normal elastomer are injection moulded to one another.

17. A method for the production of the primary packaging container of claim 1, the method comprising:
producing a first of the hollow body and the closure;
injection moulding a second of the hollow body and the closure so that the closure closes the opening and the normal elastomer connects to the hollow body.

18. An apparatus comprising:
a hollow body having an opening, the hollow body comprising a cycloolefin polymer or a cycloolefin copolymer;
a single dose of a therapeutic substance and/or a diagnostic substance in the hollow body; and
a closure being made of a normal elastomer and a thermoplastic elastomer layer over the normal elastomer defining a continuous puncture region therethrough, the closure closing the opening with the puncturing region at the opening, the puncturing region configured to allow introduction of a cannula into the hollow body, the normal elastomer being connected to the hollow body so that the normal elastomer and hollow body are inseparable from one another without damage to the normal elastomer and/or the hollow body.

19. The primary packaging container of claim 1, wherein the closure and the hollow body are not separable in a non-destructive manner so that upon separation, residue of one of the hollow body or the closure remains on the other one of the hollow body or the closure.

20. The primary packaging container of claim 1, wherein the opening comprises a circumferentially groove, and wherein the closure connects to the hollow body in the groove so that a top, bottom and side surface of the closure are connected to the hollow body.

21. The primary packaging container of claim 1, wherein the hollow body comprises a top surface having a first portion and a second portion, and wherein the opening is defined through the first portion and the closure connects to the hollow body at the second portion.

22. The primary packaging container of claim 1, wherein the hollow body comprises a flanged rim at the opening, the flanged rim having lateral surfaces, and wherein the normal elastomer covers at least a portion of the lateral surfaces of the flanged rim.

23. A primary packaging container for receiving a pharmaceutical product, comprising:
a hollow body having an opening, the hollow body comprises a cycloolefin polymer or a cycloolefin copolymer; and
a closure having a puncturing region, the closure closing the opening with the puncturing region at the opening, the puncturing region being configured to allow introduction of a cannula into the hollow body and resealing the hollow body upon withdrawal of the cannula,
wherein the closure comprises an elastomer that connects the closure and the hollow body together so that the closure and the hollow body are not separable in a non-destructive manner,
wherein the hollow body comprises an outer side, wherein the outer side lacks a flanged rim at the opening and has at least one form-fitting element that is configured for receipt in a device, and wherein the elastomer of the closure is a normal elastomer and the closure further comprises a layer of thermoplastic elastomer over the normal elastomer.

\* \* \* \* \*